United States Patent
Fuchs et al.

(10) Patent No.: US 7,109,490 B2
(45) Date of Patent: Sep. 19, 2006

(54) METHOD AND MEDICAL DEVICE DESIGNED FOR IMPLEMENTING THIS METHOD

(75) Inventors: Theobald Fuchs, Nürnberg (DE); Willi Kalender, Möhrendorf (DE); Tillman Riess, Güllstr (DE); Quirin Spreiter, Erlangen (DE); Thomas von der Haar, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 251 days.

(21) Appl. No.: 10/488,398

(22) PCT Filed: Aug. 21, 2002

(86) PCT No.: PCT/DE02/03056

§ 371 (c)(1),
(2), (4) Date: Mar. 3, 2004

(87) PCT Pub. No.: WO03/024332

PCT Pub. Date: Mar. 27, 2003

(65) Prior Publication Data

US 2004/0222380 A1   Nov. 11, 2004

(30) Foreign Application Priority Data

Sep. 3, 2001   (DE) .................................. 101 43 045

(51) Int. Cl.
*G01T 1/20* (2006.01)
*G01T 1/166* (2006.01)

(52) U.S. Cl. .................................. 250/369; 250/363.04
(58) Field of Classification Search ................. 250/369, 250/363.04
See application file for complete search history.

(56) References Cited

U.S. PATENT DOCUMENTS 4,178,510 A   12/1979   Wagner
4,280,178 A   7/1981   Nassi et al.

FOREIGN PATENT DOCUMENTS

| DE | 26 27 885 A1 | 1/1978 |
| DE | 199 21 763 A1 | 11/2000 |
| EP | 0 24 698 B1 | 3/1981 |
| EP | 0 109 205 A2 | 5/1984 |
| EP | 0 404 118 A2 | 12/1990 |

OTHER PUBLICATIONS

Willi A. Kalender, "Computed Tomography—Fundamentals, System Technology, Image Quality, Applications", Preface and pp. 150-161.

*Primary Examiner*—David Porta
*Assistant Examiner*—Mindy Vu
(74) *Attorney, Agent, or Firm*—Harness, Dickey & Pierce

(57) ABSTRACT

A method is for restoring a signal of a defective channel of a beam detector, which has a multitude of channels and by means of which projections are recorded from different directions of projection. The channels of the beam detector each have a detector element with channel electronics connected downstream therefrom. The signal of the defective channel is restored while using neighboring signals of an M-neighborhood of the same projection and from adjacent signals of an M-neighborhood of additional projections.

Figure 1:
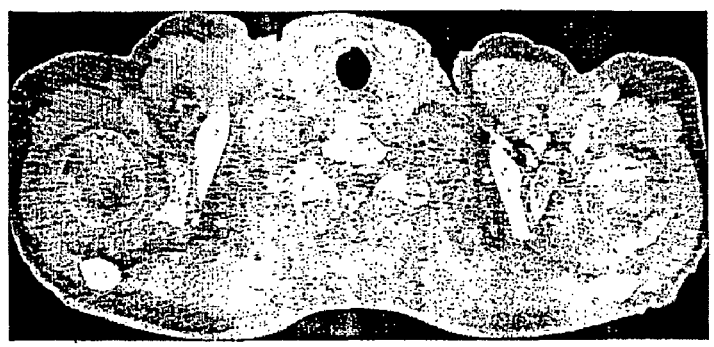
Figure 1:
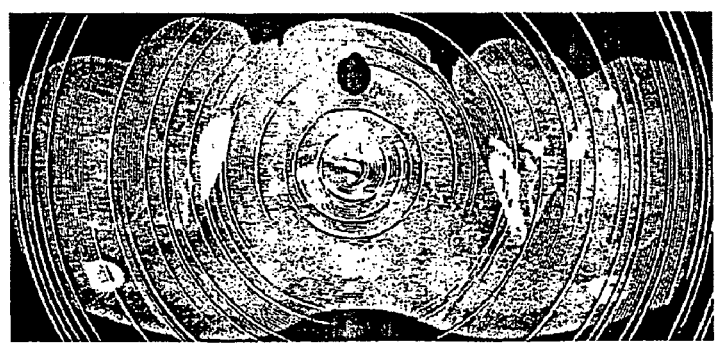
Figure 1:
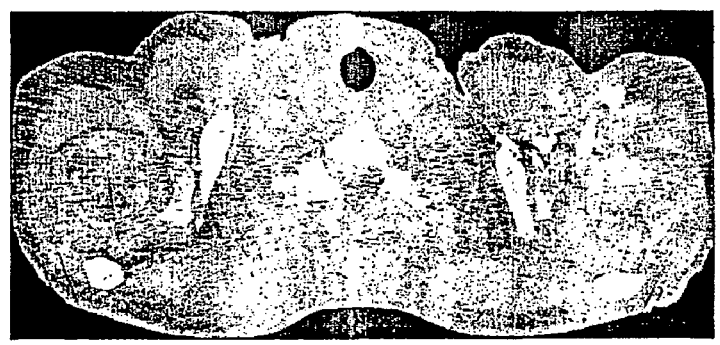
Figure 1:
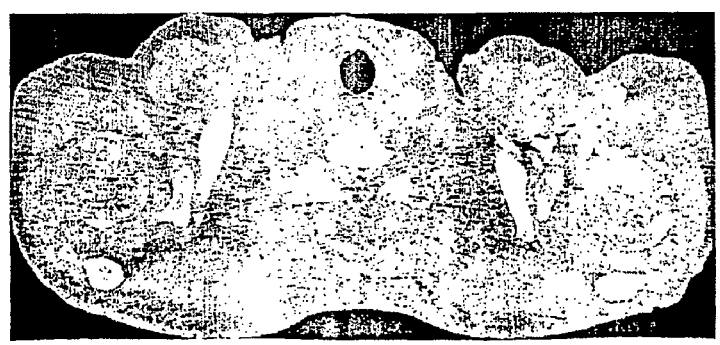

18 Claims, 5 Drawing Sheets a b c d

METHOD AND MEDICAL DEVICE DESIGNED FOR IMPLEMENTING THIS METHOD

This application is the national phase under 35 U.S.C. § 371 of PCT International Application No. PCT/DE02/03056 which has an International filing date of Aug. 21, 2002, which designated the United States of America and which claims priority on German Patent Application number DE 101 43 045.0 filed Sep. 3, 2001, the entire contents of which is hereby incorporated herein by reference.

FIELD OF THE INVENTION

The invention generally relates to a method for restoring a signal of a defective channel of a radiation detector that has a multiplicity of channels and/or by which projections from different projection directions are recorded, and/or whose channels in each case have a detector element with a downstream channel electronic unit. The invention also generally relates to a medical device, in particular a CT (computer tomography) device, designed for implementing this method.

BACKGROUND OF THE INVENTION

In medical diagnostics, for example, computer tomography serves the purpose of producing non-overlapping tomographs. In the case of x-ray computer tomography, these tomographs are calculated with the aid of a computer from data that are recorded during the circular or spiral revolution of an x-ray tube and a suitable detector about the patient (see Kalender, W. A.: Computertomographie. Grundlagen, Gerätetechnologie, Bildqualität, Anwendungen. [Computer tomography. Fundamentals, equipment technology, image quality, applications.] Publicis MCD Verlag, Munich, 2000). The aim is to obtain tomographs in the shortest possible time.

Because of their excessively slow data collection rate, conventional CT devices having a so-called single-row detector, that is to say a detector that has a single detector row or row-type arrangement of detector elements, are not capable of meeting the growing clinical demands (high-resolution recording of complete organs during a pause in breath, large-volume angiographs, three-dimensional representations of anatomical structures with isotropic and high resolution).

Although it would be possible to increase the data collection rate by reducing the time of revolution of the x-ray tube and detector, mechanical limits are soon encountered in so doing. In order, nevertheless, to permit a further increase in the data collection rate, CT devices have recently been developed which have a so-called multirow detector, that is to say a detector that has several rows, for example 4 rows, of detector elements (see Kalender loc. Cit.).

A data collection rate that is further increased by way of so-called area detectors, that is to say multirow detectors with a high number of rows (for example 64 detector rows) is being aimed at, and is the subject matter of the current development.

If a detector channel has defects or is entirely defective, its corrupted or missing signal leads to inconsistencies in the total data volume that have a disadvantageous effect on the quality of the reconstructed tomographs. For example, depending on the number of channels affected and on the type of defect, annular to linear artifacts appear that cover structures in the object being examined. In the most favorable case, they are merely perceived as disturbing by the viewer. But frequently, they influence the diagnosis disadvantageously or even render it entirely impossible.

FIG. 1a illustrates a tomograph of the shoulder area of a human patient recorded by a CT device with an entirely intact detector. If, for example, 64 of 2688 channels of the detector are defective, a tomograph in accordance with FIG. 1b may result. In this case, it is severely affected by artifacts in the case in which the defective channels have a constant signal level in each case independently of the number of x-ray quanta actually impinging on the corresponding detector element. For the sake of simplicity, the term defective channel will always be used below independently of whether a channel is entirely defective or only operating in a defective way.

The cause of a defective channel can be both defects in the actual detector element itself, and defects in the downstream electronic signal processing unit. Consequently, a defect can be eliminated by exchanging the relevant detector element and/or the relevant part of the electronic signal processing unit. Such an exchange is, however, time-consuming and costly.

Methods have therefore been developed that render it possible to restore the signals of defective channels in order thus to be able to dispense with an exchange, or to be able to delay the latter at least until no interruption of the operation of the CT device is necessary. Instead of the tomograph in accordance with FIG. 1b, the application of a correction method known from DE 199 21 763 A1 results in the tomograph in accordance with FIG. 1c which, although clearly having fewer artifacts, is far from being free of artifacts.

In the case of multirow detectors with N rows, the number of the channels is N times the number of the channels present in the case of a single-row detector. In the case of multirow detectors, in particular, however, in the case of area detectors, the probability of a defect therefore rises by at least N times compared with a single-row detector. The economic use of multi-row and area detectors is therefore brought into question because of the high probability of frequently having to exchange detector elements or parts of the electronic signal processing unit.

SUMMARY OF THE INVENTION

It is an object of an embodiment of the invention to create the preconditions for a practical and economic use of multirow and area detectors by specifying a method, suitable for such detectors, for restoring the signal of a defective channel, and a medical device for implementing such a method.

Consequently, a signal to be restored is restored from the adjacent signals of the respective current and at least one further projection.

Since recourse is also made to signals of at least one further projection, a particularly realistic restoration is achieved with the consequence that, as a rule, neither do disadvantageous influences arise for the diagnosis, nor are artifacts perceived as disturbing or irritating by the viewer visible in the tomograph determined by using the restored signals. Further, this situation is achieved without the need to exchange the defective channel or channels. Since the method accesses signals already present, it operates quickly enough to be able to be used even in the case of high data collection rates or short cycle times of the x-ray tube and detector.

As may be seen from FIG. 1d, which shows a tomograph obtained with the aid of the method according to an embodiment of the invention from the same signals as for FIG. 1b, defects caused by defective or corrupted signals actually no longer appear in the reconstructed tomograph. Thus, the method according to an embodiment of the invention really does supply tomographs virtually free of artifacts.

In accordance with a variant of an embodiment of the invention, it is particularly advantageous for the purpose of restoration to make use of the data of a so-called eight neighborhood of that projection in which the signal is to be reconstructed (termed current projection below), and of the data of the eight neighborhood of the projection directly preceding the current projection in time (termed preceding projection below).

It is also possible within the scope of an embodiment of the invention to apply methods that make use of the data of extended neighborhoods, for example of twenty-four neighborhoods, and/or operate with supplementary addition of data that are in front of the preceding projection in time or after the current projection in time.

Moreover, an embodiment of the invention can also be applied in the case of devices whose detector system does not rotate about a center of rotation on a circular or spiral path relative to the object to be examined, but moves along a trajectory of another type.

The terms "current projection", "projection (directly) preceding (in time)" and "(temporally) adjacent projection" are used with regard to the circumstance that the projections are recorded following one another in time so that a data stream corresponding to the projections is produced. Consequently, adjacent projections are those projections which relate temporally, and therefore also spatially, to the current projection in such a way that the data contained in them are suitable for restoring the signal of a defective channel with reference to the current projection. As mentioned, adjacent projections can be after the current projection in time, but also in front of the (directly) preceding projection.

Figure 2:
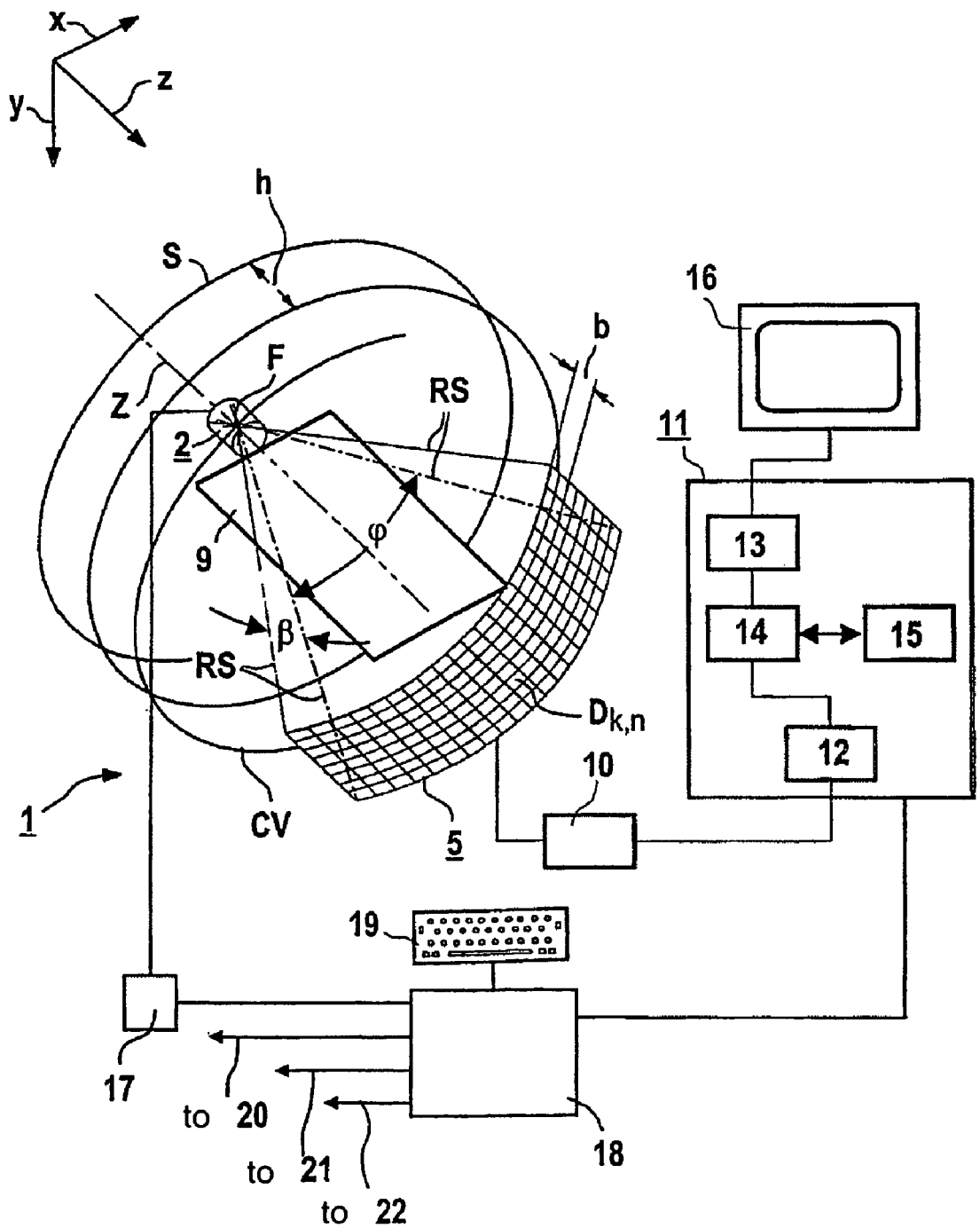
Figure 3:
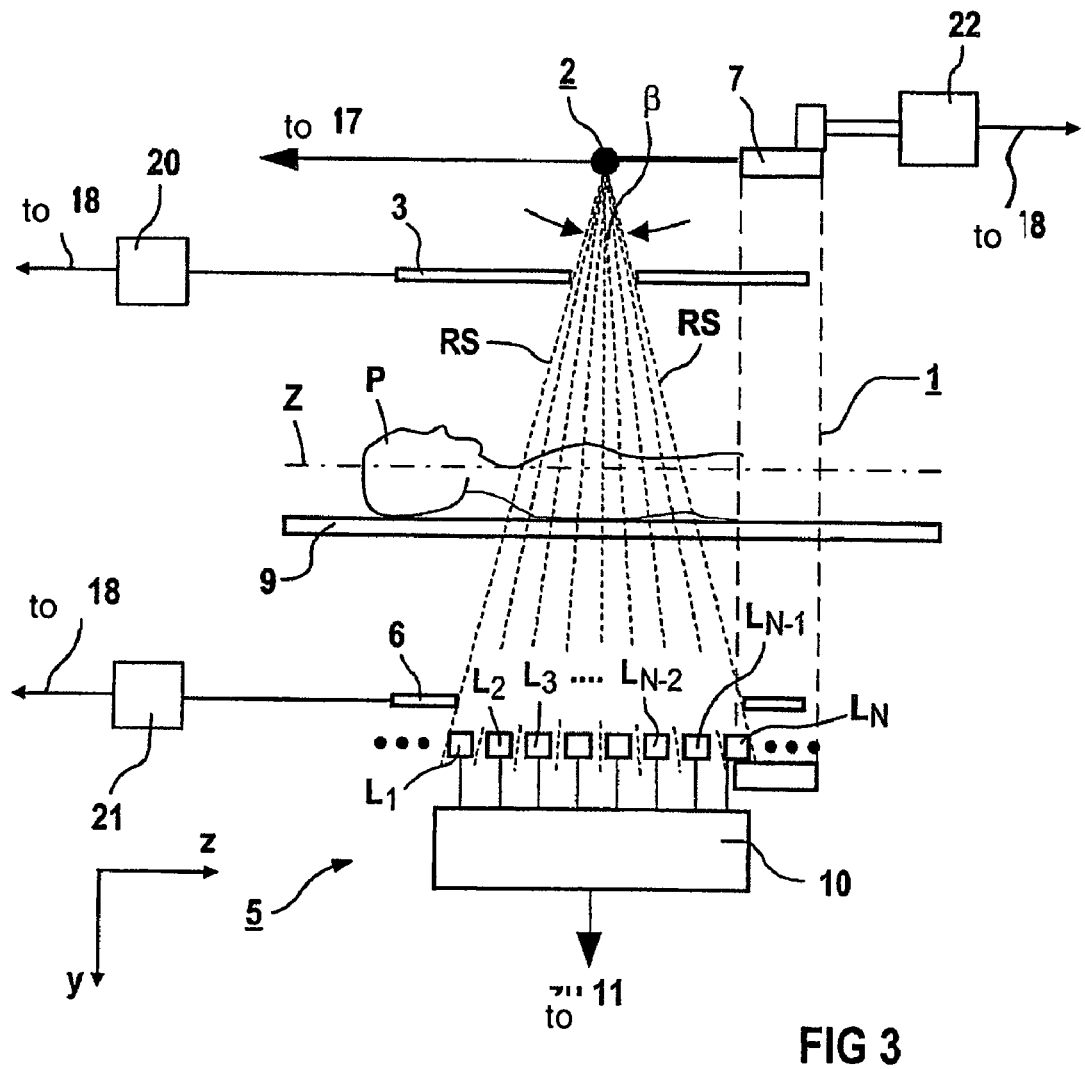
Figure 4:
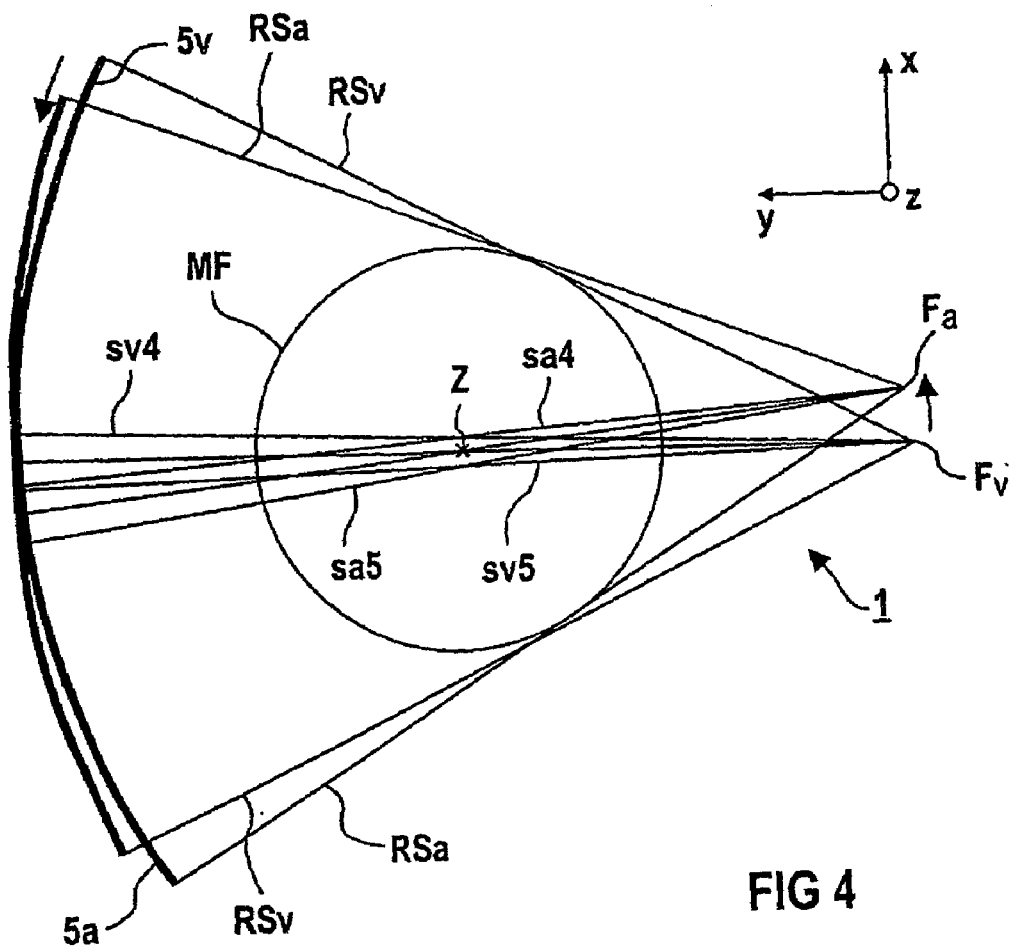
Figure 5:
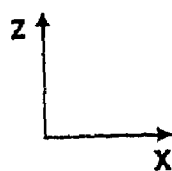
Figure 6:
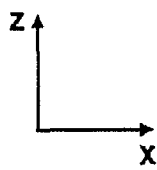
Figure 7:
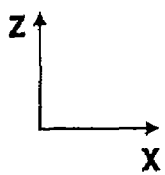

Further advantages, features and details of the invention will become evident from the description of illustrated embodiments given hereinbelow and the accompanying drawings, which are given by way of illustration only and thus are not limitative of the present invention, wherein:

FIG. 1 shows tomographs of the shoulder area of a human patient, FIG. 1a being a satisfactory tomograph, FIG. 1b being the same tomograph recorded with the aid of a detector system having several defective channels and therefore being affected by artifacts, FIG. 1c being a tomograph obtained with the aid of a known correction method from the same signals as in FIG. 1b, and FIG. 1d being a tomograph obtained with the aid of the method according to an embodiment of the invention from the same signals as in FIG. 1b, FIGS. 2 and 3 show an illustration of the principle of a device for applying the method according to an embodiment of the invention, FIG. 4 shows the geometrical relationships fundamental to the method according to an embodiment of the invention, and FIGS. 5 to 7 show the signals, used for the method, of the two projections used, and the point of origin of these signals.

DETAILED DESCRIPTION OF THE PREFERRED EMBODIMENTS

FIGS. 2 and 3 show a CT device of the third generation which is suitable for implementing the method according to an embodiment of the invention. Its measuring arrangement, denoted overall by 1, has an x-ray source, denoted overall by 2, with a radiation aperture 3 placed in front of it and close to the source (FIG. 3), and a detector system 5, constructed as a two-dimensional array of several rows and columns of detector elements—of which one is denoted in FIG. 2 by $D_{k,n}$—, with a radiation aperture 6 placed in front of it and close to the detector (FIG. 3). In FIG. 2, for reasons of clarity, only eight rows of detector elements $D_{k,n}$ are illustrated, but the detector system 5 can have further rows of detector elements $D_{k,n}$ which is indicated by dots in FIG. 3.

The x-ray source 2 with the radiation aperture 3, on the one hand, and the detector system 5 with the radiation aperture 6, on the other hand, are arranged opposite each other on a rotary frame 7 in the way to be seen from FIG. 3 and such that a pyramidal x-ray beam, which, during the operation of the CT device, originates from the x-ray source 2 and is collimated by the adjustable radiation aperture 3 and whose edge rays are denoted by RS, impinges on the detector system 5. In the process, the radiation aperture 6 is set to correspond to the cross section, set by means of the radiation aperture 3, of the x-ray beam such that only that area of the detector system 5 which can be struck directly by the x-ray beam is exposed. In the operating mode illustrated in FIGS. 2 and 3, this is eight rows of detector elements $D_{k,n}$, which are denoted active rows below. The further rows indicated by dots are covered by the radiation aperture 6 and are therefore inactive. Each row of detector elements $D_{k,n}$ has a number K of detector elements (for example K=672), k=1 to K being the so-called channel index. The active rows $L_n$ of detector elements $D_{k,n}$ are denoted by $L_1$ to $L_N$ in FIG. 3, n=1 to N being the row index.

The detector element $D_{244,7}$ is thus the detector element of the channel k=244 of the 7th detector row (n=7).

The x-ray beam has the cone angle $\beta$, plotted in FIGS. 2 and 3, which is the opening angle of the x-ray beam in a plane containing the system axis Z and the focus F. The fan angle $\phi$ of the x-ray beam, which is the opening angle of the x-ray beam in a plane lying at right angles to the system axis Z and containing the focus F, is plotted in FIG. 2.

The rotary frame 7 can be set rotating about the system axis Z by means of a drive device 22. The system axis Z runs parallel to the z axis of a three-dimensional rectangular coordinate system illustrated in FIG. 2.

The columns of the detector system 5 likewise run in the direction of the z axis, while the rows, whose width b is measured in the direction of the z axis and is 1 mm, for example, run transversely with respect to the system axis Z and the z axis.

In order to be able to bring an object to be examined, for example a patient P, into the beam path of the x-ray beam, a bearing device 9 is provided. The bearing device can be displaced parallel to the system axis Z, that is to say in the direction of the z axis. Specifically, this can be done in such a way that there is synchronization between the rotational movement of the rotary frame 7 and the translational movement of the bearing device. The effect is that the ratio between translational and rotational speed is constant. It is possible to adjust this ratio by a desired value for the feed h of the bearing device being selected per rotation of the rotary frame.

It is therefore possible for a volume of an object to be examined, which is located on the bearing device 9, to be examined in the course of volume scanning. Volume scanning may be performed in the form of spiral scanning with the effect that, with simultaneous rotation of the measuring unit 1 and translation of the bearing device 9, a large number of projections from various projection directions are recorded via the measuring unit per revolution of the measuring unit 1. During the spiral scanning, the focus F of the x-ray source moves relative to the bearing device 9 on a spiral path denoted by S in FIG. 2.

The measured data read out in parallel from the detector elements of each active row of the detector system 5 during the spiral scanning and corresponding to the individual projections are subjected to digital/analog conversion in a data conditioning unit 10, preferably arranged on the rotary frame 7, are serialized and transmitted to an image computer 11. For each of the detector elements, the data conditioning unit 10 includes, in a way not illustrated, an electronic signal processing unit downstream thereof, that is also denoted electronic channel unit.

As an alternative to spiral scanning, it is also possible to set the feed h=0, with the consequence that the focus F moves on a circular path. This mode of operation is mostly denoted tomograph scanning. In the case of tomograph scanning as well, a large number of projections from various projection directions are recorded per revolution of the measuring unit 1.

After the measured data, that is to say the projections, have been preprocessed in a preprocessing unit 12 of the image computer 11, the resulting data stream passes to a reconstruction unit 13. This unit uses the measured data to reconstruct CT images of desired layers of the object to be examined. Specifically in the case of spiral scanning using a method known per se of spiral interpolation (for example 180LI or 360LI interpolation), and using a method likewise known per se in the case of tomograph scanning.

The CT images are composed of pixels arranged in the form of a matrix. The pixels are assigned to the respective image area, with each pixel being assigned a CT number in Hounsfield Units (HU) and with the individual pixels being displayed in accordance with a CT number/gray value scale with a gray value corresponding to their respective CT number.

The tomographs reconstructed by the tomograph reconstruction unit 13 from the projections are displayed on a display unit 16, for example a monitor, connected to the image computer 11.

Since the CT device in accordance with FIGS. 2 and 3 for implementing a method according to an embodiment of the invention that is still to be described in detail is designed for restoring the signals of defective channels of the detector system 5, the image computer further has a signal restoring device 14 and a buffer 15 assigned to the latter.

The x-ray source 2, for example an x-ray tube, is supplied by a generator unit 17 with the requisite voltages and currents, for example the tube voltage U. In order to be able to set the latter to the respectively requisite values, the generator unit 17 is assigned a control unit 18 with a keyboard 19, which permits the values to be set as required.

In addition, the operation and control of the CT device apart from this is carried out by way of the control unit 18 and the keyboard 19, which is illustrated by the fact that the control unit 18 is connected to the image computer 11.

Amongst other things, the number N of the active rows of detector elements $D_{k,n}$, and therefore the position of the radiation apertures 3 and 6, can be set, for which purpose the control unit 18 is connected to the adjustment units 20 and 21 assigned to the radiation apertures 3 and 6. In addition, the rotation time τ can be set, which is the time needed by the rotary frame 7 for a complete revolution and which is illustrated by the fact that the drive unit 22 associated with the rotary frame 7 is connected to the control unit 18.

In the case of the defect of one or more of the channels of the detector system 5—the defect can be caused by the respective detector element itself and/or the channel electronic unit downstream of the latter—the signal of each defective channel is restored on the basis of the method according to an embodiment of the invention.

For this purpose, in a first mode of operation corresponding to a first variant of the method according to an embodiment of the invention, during the recording of the respectively current projection the signal of the defective channel that is entirely missing or corrupted in accordance with the defect respectively present in the current projection is restored on the basis of signals, stored in the buffer 15, of the channels, adjacent to the defective channel, of the directly preceding projection, and on the basis of the signals of the corresponding channels of the current projection. This is performed in the signal restoring device 14.

In the first mode of operation, the restoration of the signals of the defective channel is performed on the basis of the signals of an eight neighborhood (M=8) of channels directly adjacent to the defective channel D. For the purpose of simplicity, these channels are denoted in FIG. 5 only by 1 to 8, the defective channel being denoted by D. Here, the channels 4 and 5 are channels that belong to the same detector row as the defective channel D. The channels 6 to 8 belong to the detector row located in the z direction immediately in front of the detector row containing the defective channel D, while the channels 1 to 3 belong to the detector row arranged in the z direction immediately after the detector row containing the defective channel D. Thus, if the defective channel is located in the detector row $L_3$, the channels 4 and 5 are likewise situated in the detector row $L_3$, the channels 6 to 8 are situated in the detector row $L_2$, and the channels 1 to 3 are situated in the detector row $L_4$.

During the recording of the current projection, in which in accordance with FIG. 4 the focus assumes the position $F_a$ and the detector the position $5_a$, the channels of the eight neighborhood of the defective channel D supply the signals sa1 to sa8, as indicated in the left-hand part of FIG. 5. The edge beams for the current projection are denoted overall by $RS_a$ in FIG. 4 for the x-ray beam, and by sa4 and sa5 for the partial x-ray beam striking the eight neighborhood of the defective channel D. The circular measuring field covered by the x-ray beam is denoted in FIG. 4 by MF.

During the recording of the projection directly preceding the current projection, the focus and the detector assumed the positions denoted in FIG. 4 by $F_v$ and $5_v$, the associated edge beams of the x-ray beam being denoted by $RS_v$, and the associated edge beams of the partial x-ray beam being denoted by sv4 and sv5. The output signals, occurring during the recording of the projection directly preceding the current projection, of the eight neighborhood of the defective channel D are denoted in the right-hand part of FIG. 5 by sv1 to sv8. As mentioned, these signals are stored in the buffer 15.

The restoration of the signal $D_r$ of the defective channel for the current projection is performed as follows on the basis of the signals sa1 to sa8 and sv1 to sv8.

The signal restoring device 14 uses the signals of these channels in a first restoring step to calculate a preliminary correction value v using $$v = \frac{1}{6} \cdot (sa4 + sa5 + sv4 + sv5 + sf4 + sf5).$$

In order to detect the influence of object structures changing in a fashion perpendicular to the image plane (plane of the drawing in FIG. 4), the signal restoring device 14 similarly calculates preliminary correction values o and u for the detector rows above and below the row containing the defective channel:

$$o = \frac{1}{6} \cdot (sa1 + sa3 + sv1 + sv3 + sf1 + sf3).$$

$$u = \frac{1}{6} \cdot (sa6 + sa8 + sv6 + sv8 + sf6 + sf8).$$

The restored signal $D_r$ is calculated by the signal restoring device 14 from the preliminary correction values v, o and u, preferably using $$D_r = v - 0.5 \cdot (o - sa2 + u - sa7),$$

or else using $$D_r = v \cdot 0.5 \cdot [(sa2/o) + (sa7/u)].$$

In the way described above for a current projection, the procedure during the scanning operation for all the recorded projections is such as to produce a data stream that is corrected with regard to the signals of the defective channel and which the tomograph reconstruction unit 13 accesses in order to reconstruct the tomographs. That is to say, the tomographs are reconstructed by the tomograph reconstruction unit 13 on the basis of the projections containing the respectively restored signals of the defective channel and, as mentioned, are displayed on the display unit 16. The procedure is as described in this case, independently of whether spiral scanning or tomograph scanning is implemented.

As is clear from FIG. 4, the x-ray source 1 and the detector system 5 move jointly on a spiral or circular trajectory about the system axis Z. The system z axis is perpendicular to the plane of the drawing in FIG. 4. The signals of the individual projections are detected in each case in an angular position, differing from the directly preceding projection, of the connecting line of the focus F and the middle of the detector 5.

The method according to an embodiment of the invention utilizes this further movement of the focus F and the detector system 5 from projection to projection. Specifically, this further movement and the use of signals from the neighborhood of the defective channel of the respective current projection and the respective directly preceding projection firstly permit the restoration, that is to say approximation, of the signal of the defective channel by way of mean values from adjacent signals in the way described. This ensures that the beam path on which the adjacent signals are based deviates on average as little as possible, owing to the object to be examined, from the beam path belonging to the defective channel D.

Each contribution, resulting from the beam path of the x radiation from the focus F to the defective channel, to the attenuation of the initial intensity of the x radiation originating from the focus F is therefore approximated particularly well by contributions of the signals, used for averaging, of the channels from the neighborhood of the defective channel D. The basis in this case is the selection of those neighboring channels of a defective channel that are located in the same detector row and for which the mean distance of the connecting line from the location of the tube focus at the instant of the recording of the projection to the middle of the channel from the connecting line from the location of the tube focus to the defective channel of the current projection is smallest.

This results overall in the most accurate approximation possible. An approximation of even only approximately similar accuracy would be impossible without the utilization of the further movement described or without the use of signals from the current projection and at least one further projection—directly preceding projection in the case of the mode of operation described.

Thus, the existence of uncorrupted signals of the channels of the eight neighborhood of the defective channel is presupposed in the restoring variant shown.

The buffer 15 can be very small in the first mode of operation, since it is always only the data of the respective preceding projection that must be present and are able, after the correction of the data of the current projection, to be overwritten thereby, since these data for their part constitute the data of the preceding projection for the correction of the next (current) projection.

In the case of an alternative second mode of operation that can be selected by way of the keyboard 19, a variant of an embodiment of the invention is applied for which the signal of the defective channel is restored in a way similar to the first mode of operation but, in accordance with FIG. 6, by using three temporally adjacent projections. This variant can be applied for restoring signals of defective channels of the average projection viewed in terms of time. Thus, the signals sf1 to sf8 are additionally taken into account then.

Mean values over the corresponding six signals of the respective detector row are again to be formed in each case for v, o and u.

The preliminary correction value v is calculated by the signal restoring device 14 using $$v = \frac{1}{6} \cdot (sa4 + sa5 + sv4 + sv5 + sf4 + sf5)$$

It holds for the preliminary correction values o and u that:

$$o = \frac{1}{6} \cdot (sa1 + sa3 + sv1 + sv3 + sf1 + sf3)$$

$$u = \frac{1}{6} \cdot (sa6 + sa8 + sv6 + sv8 + sf6 + sf8).$$

The restored signal $D_r$ is calculated by the signal restoring device 14 from the preliminary correction values v, o and u, preferably in a way similar to the variant described above, using $$D_r = v - 0.5 \cdot (o - sa2 + u - sa7)$$

or using $$D_r = v \cdot 0.5 \cdot [(sa2/o) + (sa7/u)].$$

In the case of a third mode of operation, which can be selected by way of the keyboard 19 as a further alternative, a variant of an embodiment of the invention is applied in which the signal of the defective channel is restored by using the signals of a twenty-four neighborhood (M=24) on the basis of the respectively current projection and the projection preceding the latter.

Consequently, in accordance with FIG. 7 signals sa9 to sa24 and sv9 to sv24 are also taken into account. Assuming that the defective channel is situated in the detector row $L_3$, signals sa23, sa4, sa5 and sa15 as well as sv23, sv4, sv5 and sv15 belong to the channels 23, 4, 5 and 15 likewise situated in the detector row $L_3$. Signals sa22, sa6, sa7, sa8 and sa16 as well as sv22, sv6, sv7, sv8 and sv16 belong to the channels 22, 6, 7, 8 and 16 situated in the detector row $L_2$; signals sa21, sa20, sa19, sa18 and sa7 as well as sv21, sv20, sv19, sv18 and sv17 belong to the channels 21, 20, 19, 18 and 17 situated in the detector row $L_1$. By contrast, signals sa24, sa1, sa2, sa3 and sa14 as well as sv24, sv1, sv2, sv3 and sv14 belong to the channels 24, 1, 2, 3 and 14 situated in the detector row $L_4$; signals sa9, sa10, sa11, sa12 and sa13 as well as sv9, sv10, sv11, sv12 and sv13 belong to the channels 9, 10, 11, 12 and 13 situated in the detector row $L_5$.

The signal restoring device 14 calculates the preliminary correction value v from the signals of these channels using $$v=0.125 \cdot (sv23+sv4+sv5+sv15+sa23+sa4+sa5+sa15).$$

In order to detect the influence of object structures changing in a fashion perpendicular to the image plane (plane of the drawing in FIG. 4), there is now a need for four preliminary correction values o, p and u, w for the detector rows situated in the z direction before and after the detector row containing the defective channel:

$$o=0.125 \cdot (sv9+sv10+sv12+sv13+sa9+sa10+sa12+sa13)$$

$$p=0.125 \cdot (sv24+sv1+sv3+sv14+sa24+sa1+sa3+sa14)$$

$$u=0.125 \cdot (sv22+sv6+sv8+sv16+sa22+sa6+sa8+sa16)$$

$$w=0.125 \cdot (sv21+sv20+sv18+sv17+sa21+sa20+sa17+sa17).$$

The signal restoring device 14 calculates the restored signal $D_r$ from the preliminary correction values v, o, p, u and w preferably using $$D_r = v - 0.5 \cdot \left( \frac{o+p}{2} - \frac{sa2+sa11}{2} + \frac{w+u}{2} - \frac{sa7+sa19}{2} \right)$$

or using $$D_r = v \cdot 0.5 \cdot \left( \frac{sa2+sa11}{o+p} + \frac{sa7+sa9}{w+u} \right)$$

The third mode of operation can also be modified in a way similar to the second mode of operation to the effect that signals of a projection directly following the current projection are also incorporated into the correction in addition to the signals of the projection directly preceding the current projection.

In the exemplary embodiments described, the influence of signals of neighboring detector rows is taken into account in each case with a weighting factor of one. However, it is also possible to apply weighting factors of less than one that take account of the distance, measured in the z direction, of the respective detector row from the detector row containing the defective channel, the weighting factor being smaller the larger the distance.

Signals of only one defective channel are restored in the case of the exemplary embodiment described. In a similar way, it is also possible to restore the signals of several defective channels, the precondition for the applicability of the invention being that each defective channel is surrounded by a neighborhood of intact channels that exhibits the size respectively used.

Within the scope of an embodiment of the invention, the detector elements can be both detector elements that convert the radiation quanta occurring directly into electrical signals, and detector elements that convert the radiation quanta occurring into electrical signals indirectly with the aid of a scintillator and a photodiode arrangement.

In the case of the exemplary embodiments described, the relative movement between the measuring unit 1 and the bearing device 9 is produced in each case by the bearing device 9 being displaced. However, the possibility also exists within the scope of the invention of letting the bearing device 9 be fixed and displacing the measuring unit 1 instead of this. The possibility also exists within the scope of an embodiment of the invention of producing the requisite relative movement by displacing both the measuring unit 1 and the bearing device 9.

The conical x-ray beam has a rectangular cross section in the case of the exemplary embodiment described. However, other cross-sectional geometries are also possible within the scope of an embodiment of the invention.

A CT device of the third generation is used in conjunction with the exemplary embodiments described above, that is to say the x-ray source and the detector system are jointly displaced about the system axis during imaging. However, to the extent that the detector system is a multirow array of detector elements, an embodiment of the invention can also be used in conjunction with CT devices of the fourth generation, in the case of which only the x-ray source is displaced about the system axis and cooperates with a fixed detector ring.

To the extent that the detector system has a multirow array of detector elements, the method according to an embodiment of the invention can also be used in the case of CT devices of the fifth generation, that is to say CT devices in which the x radiation originates not only from one focus, but from several foci of one or more x-ray sources displaced about the system axis.

The CT device used in conjunction with the above-described exemplary embodiments has a detector system with detector elements arranged in the manner of an orthogonal matrix. However, an embodiment of the invention can also be used in conjunction with CT devices whose detector system has detector elements arranged in another way as a two-dimensional array.

The exemplary embodiments described above relate to the medical application of an embodiment of the invention. However, the invention can also be applied outside of medicine, for example, in nondestructive materials testing by means of a CT device.

The exemplary embodiments described are to be understood merely as exemplary, in particular including with regard to the design of the image computer 11 described. For example, the signal restoring unit 14 and the buffer 15 can also be components of a separate computer unit.

It may be stated in summary that an embodiment of the invention makes available a correction method with the aid of which it is possible to restore signals of defectively operating or entirely defective channels of the data recording system of a medical device, in particular a CT device: the signal of a detector channel that is operating defectively during a projection or is entirely defective is calculated from the signals of the channels of the same projection that are adjacent to the channel, and from the corresponding signals of the projection or projections preceding this projection in time and/or following it in time. The calculation can be performed, for example, using a signal restoring device and a buffer device.

It is therefore possible, in particular, to operate a CT device, in particular in medical diagnostics, despite defective channels with the least possible loss in quality of the reconstructed tomographs, and/or to continue operation after the occurrence of a defect. The tomographs reconstructed on the basis of projections containing restored signals can be evaluated very well and are free of disturbing image artifacts even if the signals of individual detector elements are entirely missing.

Exemplary embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

The invention claimed is:

1. A method for restoring a signal of a defective channel of a radiation detector, comprising:

recording projections from different projection directions in a multiplicity of channels of the radiation detector, wherein the channels each include a detector element with a downstream channel electronic unit; and restoring the signal of the defective channel by using adjacent signals of an M neighborhood of the same projection and from adjacent signals of an M neighborhood of further projections, wherein the signal of the defective channel is restored from signals of the same projection and a projection directly preceding in time.

2. The method as claimed in claim 1, wherein the signal of the defective channel is restored by using adjacent signals of at least one of an eight (M=8) and twenty-four neighborhood (M=24).

3. The method as claimed in claim 2, wherein the signal of the defective channel is restored from signals of the same projection, of the projection directly preceding time, and of the projection directly following in time.

4. The method as claimed in claim 2, wherein at least one of signal values and preliminary correction values required for restoring the signal of the defective channel are provided with a weighting factor.

5. The method as claimed in claim 4 for restoring a signal of a defective channel of a radiation detector that has several detector rows with several detector elements, wherein the weighting factor is selected in accordance with a distance of a respective detector row from the detector row including the defective channel.

6. A medical device comprising:

an image computer implementing the method as claimed in claim 2.

7. The method as claimed in claim 1, wherein the signal of the defective channel is restored from signals of the same projection, of the projection directly preceding time, and of the projection directly following in time.

8. The method as claimed in claim 1, wherein the radiation detector includes several detector rows with several detector elements, and wherein the signal of the defective channel is restored with aid of a preliminary correction factor µ from channels nearest the same detector row of the same projection, and from corresponding channels of the same detector row of one or more temporally adjacent projections, and with aid of two preliminary correction values o and u of the same and at least one temporally adjacent projections, o and u being calculated from signals of the detector rows adjacent to the detector row containing the defective channel.

9. The method as claimed in claim 1, wherein at least one of signal values and preliminary correction values required for restoring the signal of the defective channel are provided with a weighting factor.

10. The method as claimed in claim 9 for restoring a signal of a defective channel of a radiation detector that has several detector rows with several detector elements, wherein the weighting factor is selected in accordance with a distance of a respective detector row from the detector row including the defective channel.

11. The method as claimed in claim 1, wherein the signal of the defective channel is restored by way of a signal restoring device having a buffer.

12. A medical device, comprising:

an image computer implementing the method as claimed in claim 1.

13. The medical device as claimed in claim 12, wherein the medical device a CT device.

14. A method for restoring a signal of a defective channel of a radiation detector, comprising:

recording projections from different projection directions in a multiplicity of channels of the radiation detector, wherein the channels each include a detector element with a downstream channel electronic unit; and restoring the signal of the defective channel by using adjacent signals of an M neighborhood of the same projection and from adjacent signals of an M neighborhood of further projections, wherein the signal of the defective channel is restored from signals of at least one of several projections preceding in time and of several projections following in time.

15. The method as claimed in claim 14, wherein the signal of the defective channel is restored by using adjacent signals of at least one of an eight (M=8) and twenty-four neighborhood (M=24).

16. The method as claimed in claim 14, wherein the radiation detector includes several detector rows with several detector elements, and wherein the signal of the defective channel is restored with aid of a preliminary correction factor µ from channels nearest the same detector row of the same projection, and from corresponding channels of the same detector row of one or more temporally adjacent projections, and with aid of two preliminary correction values o and u of the same and at least one temporally adjacent projections, o and u being calculated from signals of the detector rows adjacent to the detector row containing the defective channel.

17. The method as claimed in claim 14 for restoring a signal of a defective channel of a radiation detector that has several detector rows with several detector elements, wherein the weighting factor is selected in accordance with a distance of a respective detector row from the detector row including the defective channel.

18. The method as claimed in claim 14, wherein the signal of the defective channel is restored by way of a signal restoring device having a buffer.

* * * * *